United States Patent
Gulati

(10) Patent No.: US 10,658,076 B2
(45) Date of Patent: May 19, 2020

(54) SYSTEM AND METHOD FOR INCREASING EFFICIENCY OF MEDICAL LABORATORY DATA INTERPRETATION, REAL TIME CLINICAL DECISION SUPPORT, AND PATIENT COMMUNICATIONS

(71) Applicant: Peter Gulati, Colleyville, TX (US)

(72) Inventor: Peter Gulati, Colleyville, TX (US)

( * ) Notice: Subject to any disclaimer, the term of this patent is extended or adjusted under 35 U.S.C. 154(b) by 111 days.

(21) Appl. No.: 16/155,805

(22) Filed: Oct. 9, 2018

(65) Prior Publication Data

US 2019/0108898 A1    Apr. 11, 2019

Related U.S. Application Data

(60) Provisional application No. 62/569,620, filed on Oct. 9, 2017.

(51) Int. Cl.
| | | |
|---|---|---|
| *G16H 10/60* | (2018.01) | |
| *G16H 50/20* | (2018.01) | |
| *G16H 15/00* | (2018.01) | |
| *G16H 10/40* | (2018.01) | |
| *G16H 50/70* | (2018.01) | |

(52) U.S. Cl.
CPC .......... *G16H 10/60* (2018.01); *G16H 10/40* (2018.01); *G16H 15/00* (2018.01); *G16H 50/20* (2018.01); *G16H 50/70* (2018.01)

(58) Field of Classification Search
CPC ........ G06Q 50/22; G06Q 50/24; G06F 19/30; G06F 19/32; G06F 19/324; G06F 19/325; G06F 19/34; G16H 10/60; G16H 10/40; G16H 50/20; G16H 50/70; G16H 15/00
USPC .......................................................... 705/2, 3
See application file for complete search history.

(56) References Cited

U.S. PATENT DOCUMENTS

| | | | | |
|---|---|---|---|---|
| 4,315,309 | A * | 2/1982 | Coli ....................... | G06Q 50/24 705/3 |
| 7,379,885 | B1 * | 5/2008 | Zakim .................... | G06F 19/325 705/2 |
| 2006/0278242 | A1 * | 12/2006 | McGlennen ........... | G16H 10/40 128/898 |
| 2011/0257988 | A1 * | 10/2011 | Denekamp ............. | G06Q 50/22 705/2 |
| 2014/0279746 | A1 * | 9/2014 | De Bruin ................ | A61B 5/00 706/12 |
| 2016/0232310 | A1 * | 8/2016 | Dunn ..................... | G06Q 30/04 |
| 2016/0357936 | A1 * | 12/2016 | Ghouri ................... | G16H 10/60 |
| 2017/0277841 | A1 * | 9/2017 | Shankar ................ | G06F 19/326 |
| 2017/0364655 | A1 * | 12/2017 | Farooqi ................. | G06F 19/00 |
| 2018/0025303 | A1 * | 1/2018 | Janz .................... | G06Q 10/0639 705/2 |
| 2019/0000350 | A1 * | 1/2019 | Narayan ................ | G16H 50/50 |
| 2019/0108912 | A1 * | 4/2019 | Spurlock, III ......... | G06N 20/10 |

* cited by examiner

*Primary Examiner* — Jason S Tiedeman
(74) *Attorney, Agent, or Firm* — Barry K. Shelton

(57) ABSTRACT

A system and method are disclosed for enhancing the efficiency and accuracy of analysis and interpretation of medical diagnostic laboratory test data for real-time clinical decision support, utilizing artificial intelligence techniques to automatically improve analytical performance and enhance provider and patient communications.

20 Claims, 5 Drawing Sheets

SYSTEM AND METHOD FOR INCREASING EFFICIENCY OF MEDICAL LABORATORY DATA INTERPRETATION, REAL TIME CLINICAL DECISION SUPPORT, AND PATIENT COMMUNICATIONS

CROSS-REFERENCE TO RELATED APPLICATIONS

The present application claims the benefit of the filing date of U.S. Provisional Patent Application No. 62/569,620, filed 9 Oct. 2017, the contents of which are hereby incorporated by reference.

BACKGROUND OF THE INVENTION

1. Field

The present invention relates generally to improving medical safety, efficiency and time management, reducing medical practice and system expenses, and more particularly, to a system and method for intelligent and enhanced laboratory data reporting, with diagnostic interpretations and recommendations as well as evidence-based recommendations for clinical actions. Among the many benefits provided by the inventions disclosed herein are improved medical diagnostic test utilization, service efficiency, increased meaningful use of EHR (electronic health records) technologies, and improved patient experience and satisfaction, all of which improve healthcare operations and patient outcomes in both outpatient and inpatient (hospital) practice settings.

2. Description of the Related Art

The state of the art in health care in the United States for medical analytic testing is marked by inefficiencies and archaic practices that have changed little over the last several decades, despite all the medical advances over that same period. FIG. 1 illustrates the prior art analytic cycle for medical testing, comprised of pre-analytic, analytic, and post-analytic phases. The first step in the pre-analytic phase is step 110, in which a physician or clinician orders a specific test or battery of tests for a patient. In step 120, the analytic test is performed, typically by collecting one or more specimens from the patent, e.g., a blood draw or urine specimen. The analytic phase consists of step 130, in which the analytic test is performed, typically by an analytic testing laboratory, as is known in the art. The post-analytic phase begins with step 140, in which the analytic test results are returned to the clinician who ordered the test. The testing center typically returns test results either in paper form or by faxing test results to the clinician's office. In step 150, the clinician reviews and analyzes the test results and any other documents regarding the analytic test performed. The patient is notified of the test results in step 160, usually by phone or mail. As part of step 160 the clinician may decide on a specific follow-up plan for the patient based on the test results, using the clinician's experience, knowledge and skill. Finally, in step 170 the patient is monitored through the follow-up plan devised by the clinician.

There are several problems in the prior art analytic cycle. First, the analytic cycle does not take advantage of the many advances made in computer processing and communications made in the last two decades. For example, analytic test results are primarily delivered in paper form or faxed in part due to HIPAA regulations regarding patient confidentiality and privacy. Second, the analytic cycle is time-consuming and inefficient. Third, the accuracy and efficacy of the diagnosis and interpretation of the analytic test results is largely a function of the clinician's knowledge and experience, and therefore varies widely among medical professionals.

The clinical laboratory is a major source of health care data. Increasingly these data are being integrated with other data to inform health system-wide actions meant to improve diagnostic test utilization, service efficiency, and increase "meaningful use." Increasingly, much of the data created by a clinical laboratory is already coded and transmitted to electronic health records as discrete elements with meaningful flags, making it more amenable to analysis than text-based clinical histories and pathology reports. With rare exceptions, the current data reports still usually offer only three, simplistic conclusions, that being normal, high, or low, or "positive" and "negative" values. Occasionally, a reference to a journal article is included in the reporting for the clinician, for example when a lab report is returned for free and total PSA testing for prostate cancer screening. However, today there are very few systems in existence that truly provide an automated, intelligent report to providers and patients, with the breadth and scope of the inventions described herein. As health care systems are pressured to improve efficiency and reduce costs while improving patient satisfaction and clinical outcomes, such as mandates by the Centers for Medicare and Medicaid Services (CMS) "Triple Aim" goals, it will be increasingly important to leverage clinical laboratory data and advances that incorporate the expertise of the clinicians, pathologists and laboratorians that best understand diagnostic test data in the context of providing accurate, meaningful, and actionable reporting.

Global measures of diagnostic care quality are in their early infancy. National programs such as Physician Quality Reporting System (PQRS), Medicare Quality Payment Program (QPP), Merit-based Incentive Payment System (MIPS), and Health Plan Employer Data and Information Set (HEDIS), contain only a handful of diagnostic measures each, and so they cannot hope to assess in a balanced way the hundreds of thousands of diagnostic-related activities that occur today across the world of clinical medicine. Inventing new clinical quality measurement programs that are economically feasible yet have adequate breadth and balance represents an enormous challenge.

What is needed is a revolutionary new approach to medical diagnostic testing and interpretation that leverages the advances in artificial intelligence, machine learning, expert systems, and Internet-based communications to create a system and method for increasing efficiency of medical laboratory data interpretation, real time clinical decision support and provider and patient communications.

SUMMARY OF THE INVENTION

The following is a non-exhaustive listing of some aspects of the present techniques for increasing efficiency of medical laboratory data interpretation in real time clinical decision support. These and other aspects are described in the following disclosure.

The present invention is a network-based, computerized expert system for laboratory data interpretation for physicians, clinicians and other healthcare providers at the point of care for both outpatient and inpatient care settings. The expert system described herein has a rules-based framework that analyzes patient data and laboratory data and incorporates artificial intelligence technologies such as supervised machine learning algorithms and neural networks to create diagnostic impressions and clinical recommendations where appropriate. The analysis module of the present invention receives the patient demographic and laboratory result data and analyzes it to identify patterns and trends and produce diagnostic results by employing the rules engine and the knowledge base. The diagnostic impressions include actual disease states and conditions with corresponding ICD-10 codes (The International Classification of Diseases, Tenth Edition (ICD-10)) when criteria are met in whole or in part and are presented as suggestions to the ordering clinician. The clinical recommendations can include recommendations for repeat or additional reflex or reflective testing (see below), recommendations for clinical follow up, recommendations for additional studies such as advanced imaging with CT or MRI of the suspected disease process, consult with the appropriate specialist for further investigations and management, and other recommendations. Reflex testing, also known as protocol testing, occurs when an initial test result meets pre-determined criteria (e.g., positive or outside normal parameters), and the primary test result is inconclusive without the reflex or follow-up test. It is performed automatically without the intervention of the ordering physician. Reflex testing may prevent the need for additional specimen procurement from the patient. The reflex test adds valuable diagnostic information and is consistent with best medical practices. Reflective testing is a procedure in which the laboratory specialist evaluates abnormal test results and decides whether additional tests are needed. This procedure is different from reflex testing, in which a predetermined test protocol is automatically completed. Considering adding tests (or not) is not a simple process, but requires professional, medical knowledge to assess the desirability of additional and appropriate tests. Previous test results and additional patient data—ideally available via an electronic patient record—are usually needed to achieve a proper assessment.

The knowledge base or reference base contains the basic science and medical disease information categorized by body system and disease states and conditions with their corresponding ICD-10 classifications, and their correlative, abnormal pattern of laboratory findings that may include both numerical and text-based data sets. In one embodiment the knowledge base is comprised of a multidimensional array of diseases and conditions based on the ICD-10 codes and categorized by body systems. The knowledge base additionally contains a list of all reference laboratory values that correspond to the normal state as well as disease states. The knowledge base also contains normal, established reference ranges specific to the region and country using the inventive system that are used to determine the normal outputs for test reporting as well as the range, minimum, and maximum cutoff values that will trigger and interact with the rules engine of the analysis module to produce a possible list of provisional (most likely) and differential diagnoses and the severity of the clinical condition for the specific patient laboratory data set. The knowledge base contains information not only to help predict disease states and conditions with their ICD-10 classifications, it also contains varying degrees and depths of clinical recommendations that are appropriate for each condition, and severity of condition discovered to be present, taking into account multiple data points from the current testing and also from the patient's medical record as available such as but not limited to severity of the abnormality, data trends, comorbid conditions, demographics, and other factors. The knowledge base can be modified and extended through the knowledge base editor, which provides an interface not only for the operator of the inventive system disclosed herein, but also for third-party collaborators. The knowledge base editor will be overseen by human clinical experts that will have the authority to validate and modify the knowledge base. The knowledge base editor will be improved over time to include knowledge as new discoveries and advances are made over time regarding disease states. The inventive system also has self-learning capabilities and the ability to add to the knowledge base based on user feedback from providers.

The rules engine incorporates artificial intelligence algorithms that achieve nearly instantaneous interpretation of the lab results input to the inventive system. It will apply various forms of Artificial Intelligence (AI) to each data set including but not limited to Rules-based Systems, Logical Conditions, Causal Probabilistic Networks, Bayesian Networks, Neural Networks, Support Vector Machines, Genetic algorithms, Ripple Down Rules, Fuzzy Logic, and other algorithms known to those skilled in the art. In one embodiment, the rules engine implements supervised machine learning, using decision trees primarily. The decision trees are arranged from general, broad terms to very specific terms as more tests are analyzed further down the decision tree. The output of the rules engine is channeled in the analysis module and cross referenced with the data in the knowledge base, to produce a meaningful graphical, color coded, numerical and test based diagnostic impression of the test report as well as associated clinical recommendations for treatment for each case, that is output by the provider reporting engine. The rules engine can be modified and extended through the rules engine editor, which provides an interface not only for the operator of the expert system disclosed herein, but also for third-party collaborators. The rules editor will be overseen by human clinical and information technology (IT) experts who will have the authority to validate and modify the rules engine. The rules engine is also self-learning by incorporating user feedback entered by providers who may agree or disagree with the strength of the diagnostic and clinical recommendations produced by the inventive system and tracked over time. The rules engine editor users will be able to add and or modify the rule sets and AI algorithms in the rules engine over time. The inventive system also self-learns to reinforce or deemphasize the various weights of each of the algorithms, based on both new clinical research and based on user feedback from providers as described herein.

The secure data storage module of the present invention stores both identified and de-identified patient data, values, trends, reports and care gap lists, i.e., list of those patients that need follow-up treatment. In some embodiments, some or all the data stored in the data storage module is stored in the form of a cryptographic blockchain ledger. The inventive system stores all active and historical laboratory data for the patients, and may also include the following additional data that may contain numerical and textual based data: patient age, sex, date of birth, ethnicity, current and past medications list and allergies, patient's active and inactive medical diseases, diagnoses and conditions, with their corresponding ICD-10 codes, copies and findings of certain diagnostic testing, including but not limited to EKG reports and interpretations, pulmonary function test reports (PFTs) and interpretations, results of blood or urinary toxicology screenings and confirmations, copies of imaging such as x-rays, CT scans, and MRI reports and findings, patient health plan information, and pharmacy information, pharmacy prescribing history including all routine medications, and data from any state registries that collect and monitor prescription data for all Schedule II, III, IV and V controlled substances, such as the Texas Prescription Monitoring Program (PMP), or its local equivalent where the inventive system is being deployed or used. In the cases of text based patient records, the text records will be converted to time stamped, computer readable formats using Optical Character Recognition (OCR) technology. This will allow the inventive system a way to easily compare data sets against known disease states and conditions in the knowledge base. The inventive system can also search the textual data using specific keywords, disease names, ICD-10 codes and the like, to generate new searches and reports.

There are two interpretive results modules for outputting the results of the present invention, one for healthcare providers and the other for patients. The provider interface sends all the diagnostic impressions and clinical recommendations produced by the analysis module to the provider reporting engine, which disseminates the findings of the lab report using secure, HIPAA compliant, real time electronic means through a bidirectional communications path to the provider using one or more means of communication. The patient interface sends all or a subset of the diagnostic impressions and clinical recommendations produced by the analysis module to the patient reporting engine, which disseminates the findings of the lab report using secure, HIPAA compliant, real time electronic means through a bidirectional communications path to the patient using one or more means of communication.

Some aspects include a method for increasing efficiency of medical laboratory data interpretation in real time clinical decision support performed by devices with processing capability, that is, any device that contains a CPU, microprocessor, microcontroller, field-programmable gate array (FPGA), application-specific integrated circuit (ASIC) or other integrated circuit able to execute instructions implementing the invention. As non-limiting examples, such devices include computing devices, such as a desktop computer, notebook computer, server, tablet, smartphone, personal digital assistant (PDA), and other mobile device.

Some aspects include a tangible, non-transitory, machine-readable medium storing instructions that when executed by a data processing apparatus cause the computing apparatus to perform operations including the above-mentioned method.

Some aspects include a system, including: one or more processors; and memory storing instructions that when executed by the processors cause the processors to effectuate operations of the above-mentioned method.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
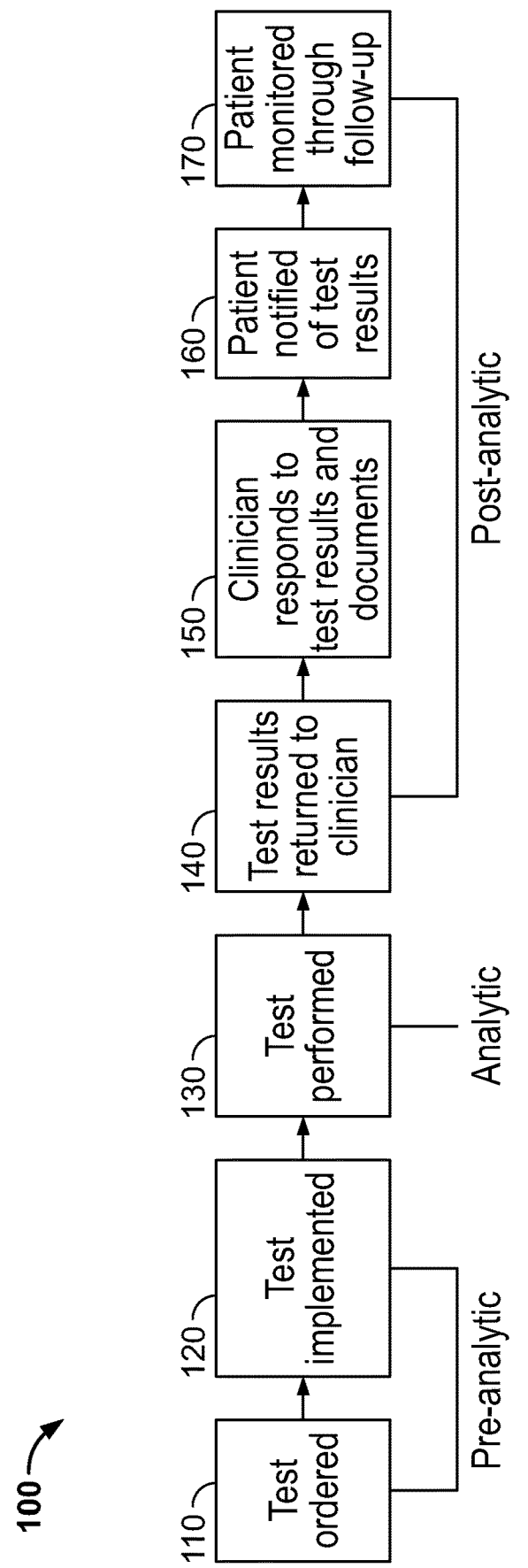
FIG. 1 depicts the prior art analytic cycle for medical testing.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF CERTAIN EMBODIMENTS

To mitigate the problems described herein, the inventor had to both invent solutions and, in some cases just as importantly, recognize problems overlooked (or not yet foreseen) by others in the fields of medical diagnostics, automated analysis of medical diagnostic results and their associated clinical implications and recommendations for further testing and or treatment. The inventive system and method are not routine, not well-understood and not conventional approaches to the problems solved by the inventions herein. Indeed, the inventor wishes to emphasize the difficulty of recognizing those problems that are nascent and will become much more apparent in the future should trends in industry continue as the inventor expects. Further, because multiple problems are addressed, it should be understood that some embodiments are problem-specific, and not all embodiments address every problem with traditional systems described herein or provide every benefit described herein. That said, improvements that solve various permutations of these problems are described below.

The present invention solves a long-standing challenge in medicine: how to use the information in diagnostic medical test results to more efficiently and accurately provide diagnoses and clinical treatment recommendations for providers and patients, in the most efficient manner possible. Prior to the inventions described herein, the process or ordering, performing and interpreting medical diagnostic tests has been a manual, inefficient and slow process that relies exclusively on the clinician's knowledge, experience and skill to provide the correct interpretation and diagnosis for the patient. The embodiments described herein provide a highly automated and efficient expert system that does not replace clinicians or physicians, but rather serves as a valuable diagnostic tool that increases the health professional's accuracy, efficiency, and efficacy in treating patients, thereby leading directly to better patient outcomes.

In the United States, the Health Insurance Portability and Accountability Act of 1996 (HIPAA) protects most individually identifiable health information held or transmitted by a covered entity or its business associate, in any form or medium, whether electronic, on paper, or oral. HIPAA's Privacy Rule calls this information protected health information (PHI) and imposes strict requirements that PHI be safeguarded. PHI is information, including demographic information, which relates to 1) the individual's past, present, or future physical or mental health condition; 2) the person vision of healthcare to the individual; or 3) the past, present, or future payment for the provision of healthcare to the individual, and that identifies the individual or for which there is a reasonable basis to believe can be used to identify the individual. Protected health information includes many common identifiers (e.g., name, address, birth date, Social Security number) when they can be associated with the health formation listed above. For example, a medical record, laboratory report, or hospital bill would be PHI because each document contain the patient's name and/or other identifying information associated with the health. Therefore, certain aspects of the present invention must ensure that PHI is stored in such a manner that protects its confidentiality. In other aspects of the present invention, PHI is de-identified, that is, processed to remove information such that the health information is not individually identifiable because it does not identify an individual and if the covered entity has no reasonable basis to believe can be used to identify an individual.

Figure 2:
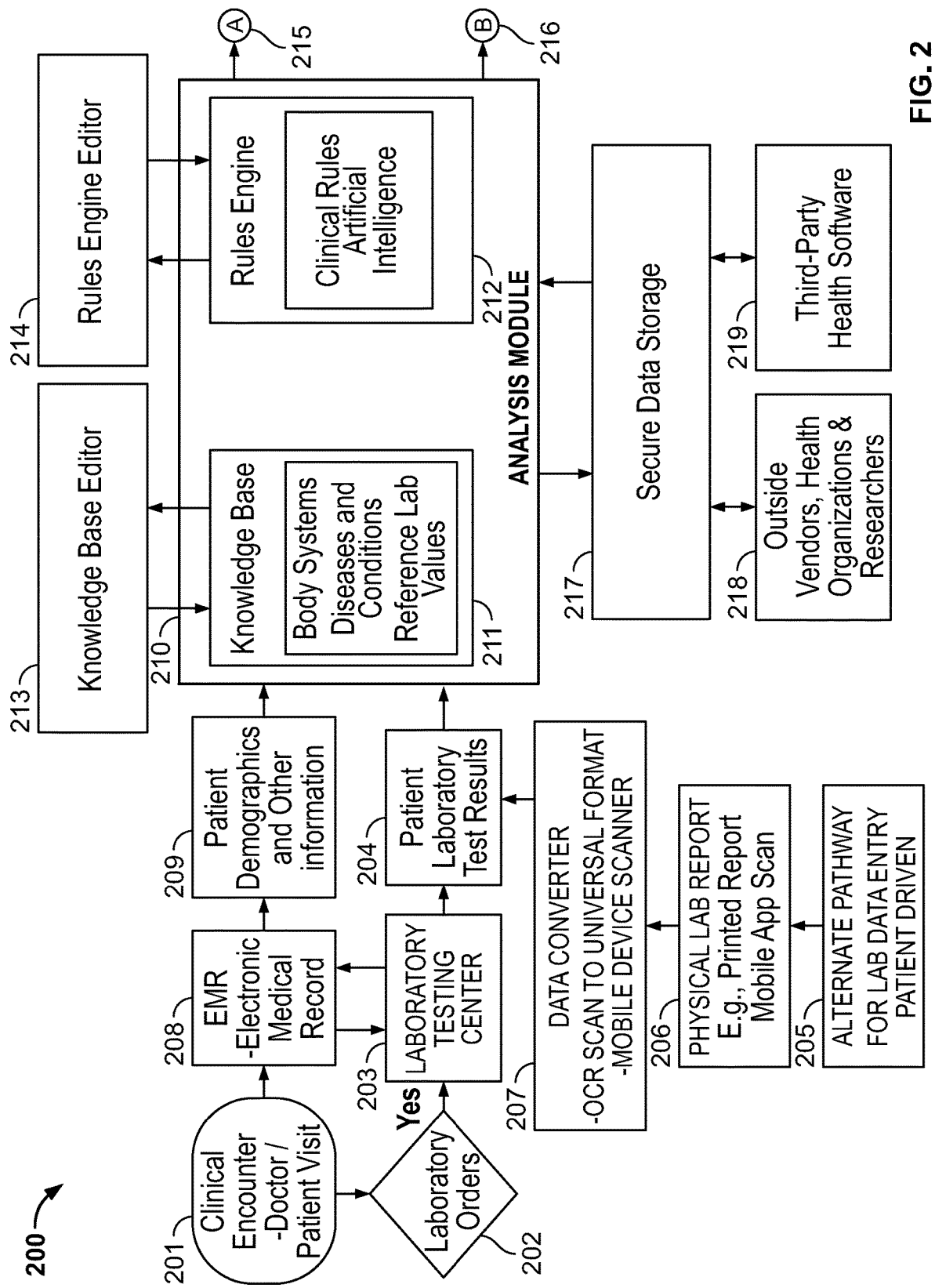
FIG. 2 is a block diagram that depicts an embodiment of the present invention comprising an analysis module with a rules engine and knowledge base that receives various inputs such as patient information, demographics and laboratory test results, and a secure data storage module for storing data used by the system.

FIG. 2 is a block diagram of an embodiment 200 of the invention that illustrates certain components such as the analysis module described herein. It should be appreciated by those skilled in the art that FIG. 2 merely illustrates one exemplary embodiment of the invention and is but one of myriad ways to accomplish the functions described herein, all of which are included within the spirit and scope of the invention. Analysis module 210 receives a variety of inputs such as patient demographic information and other patient information 209, and patient laboratory test results 204. Although certain types of information in certain formats are depicted in FIG. 2, the inventor contemplates other types of information or information in other formats, all of which are included within the spirit and scope of the invention. Generally, the inventive method starts with a clinical encounter 201, such as a doctor-patient visit in an outpatient or inpatient care setting. Often the clinician will order one or more laboratory tests 202 for the patient. Laboratory testing center 203, which is commonly a third-party laboratory testing provider but might also be associated with the clinician or hospital, performs the ordered laboratory testing of the patient, which can include the collection of blood, urine, saliva, buccal mucosa, skin biopsy, pathology specimen, and other specimens or any other ordered test. In most cases, the patient laboratory test results 204 are transmitted directly from the laboratory testing center to the analysis module of the present invention electronically. In other scenarios, depicted as alternate pathway 205 the patient receives the laboratory test results, e.g., in paper format received in the mail or via facsimile transmission. The patient takes the laboratory testing report 206 and submits it to data converter 207, which in one embodiment can be an optical character recognition (OCR) scanner that converts the testing report into a universal format recognized by analysis module 210. Another embodiment of data converter 207 is a mobile device application that can take a photo of the laboratory report to produce the universal format recognized by analysis module 210. The invention is not limited to the specific form of converting the laboratory test results into a form that is usable by analysis module 210. For example, the laboratory results data could be transmitted directly from another patient portal accessed by the patient in another system, and securely transmitted to the inventive system, in one embodiment. In addition to the laboratory test results, other information and data regarding the patient can be supplied by the clinician or physician, for example, in an electronic medical record (EMR) 208 (also known as an electronic health record or EHR), which contains patient demographics and other information 209 and is input to analysis module 210. Information that can be stored and analyzed by analysis module 210 includes not only laboratory numerical and text data, but also patient identity, age, sex, date of birth, ethnicity, current and past medications list and allergies, patient's active and inactive medical diseases, diagnoses and conditions, with their corresponding ICD-10 codes, copies and findings of certain diagnostic testing, including but not limited to EKG reports and interpretations, pulmonary function test reports (PFTs) and interpretations, results of blood or urinary toxicology screenings and confirmations, copies of imaging such as x-rays, CT scans, and MRI reports and findings, patient health plan information, and pharmacy information, pharmacy prescribing history including all routine medications, and data from any State Registries that collect and monitor prescription data for all Schedule II, III, IV and V controlled substances, such as the Texas Prescription Monitoring Program (PMP), or its local equivalent where the inventive system is being deployed or used. Moreover, the invention communicates with mobile devices as well as wearable health technologies (e.g., FitBit or Apple Watch devices) to capture as inputs relevant health data into the patient secure records, as well as the knowledge base described herein to improve the completeness and accuracy of the diagnostic impressions and clinical recommendations. Data that is automatically and wirelessly captured includes heart rate, blood pressure, blood sugar levels, EKG monitor, steps walked, and exercise activity among others. Analysis module 210 contains knowledge base 211, which contains, e.g., data regarding body systems, diseases, conditions and reference laboratory values for a variety of medical diagnostic tests. Initially the knowledge base contains a large set of information for many body systems, diseases, conditions and related reference laboratory values, and is extendable and editable using the knowledge base editor 213. The knowledge base editor permits the operator of the expert system as well as third-party collaborators to modify and add information to the knowledge base, such as systems-based classification, and edits to reference ranges for diseases and conditions, as well as the clinical recommendations data sets. In certain embodiments of the present invention, third-party experts such as clinicians, physicians and researchers provide input to the expert system's knowledge base, rules engine, or both. In some embodiments, the knowledge base is categorized by laboratory test and by body system. Analysis module 210 compares the diagnostic test results in the laboratory test results to the normal, established references and ranges that contain both numerical and textual data, to determine the possible list of differential diagnoses and the severity of the clinical condition for the specific patient laboratory data set. As a non-limiting example, common laboratory tests ordered with their Current Procedural Terminology (CPT) codes such as may be found in an adult wellness panel include: CBC 85207, CMP 80053, LIPID PANEL 80061, DIRECT LDL 83721, TSH 84443, A1c level 83036, PSA 84153, UA 81001, VITAMIN D 82306, and other tests.

FIG. 2 further shows rules engine 212 as part of the analysis module 210. Rules engine 212 applies clinical rules and artificial intelligence algorithms including Rules-based systems, Decision Trees, Logical Conditions, Causal Probabilistic Networks, Bayesian Networks, Support Vector Machines, Neural Networks, Genetic algorithms, Ripple Down Rules, Fuzzy Logic, and other algorithms known by those skilled in the art. Initially the rules engine contains a large set of clinical rules for approximately one thousand commonly ordered clinical laboratory tests as well as extensive decision trees for medical diagnosis and is extendable using the rules engine editor 214. The rules engine editor permits the operator of the expert system such as human, expert clinical and IT validators, as well as third-party collaborators to modify and add information to the rules engine as increasing data is collected by the system and processed, and new discoveries are made in the world regarding conditions and diseases both in terms of new diagnoses and classification, as well as new or revised clinical treatment guidelines that are evidence-based, such as recommendations for additional testing, treatment, or referral of the patient. Because the rules engine implements supervised machine learning by, e.g., feedback loops from users using weighted and aggregated regional responses, and neural networks and other machine learning networks, its analytical capabilities grow as the amount of data and other inputs increase over time. Moreover, user feedback regarding the accuracy, usefulness and scope of the recommendations will improve the overall system accuracy and precision of the diagnoses and clinical treatment plan recommendations made for each patient laboratory scenario over time, and this "self-learning" process incorporated into the analysis module will automatically improve the rules engine over time. Two outputs of analysis module 210 are depicted as output A 215 and output B 216, which are coupled to inputs A 302 to provider interface 301 and B 304 to patient interface 303 in FIG. 3. It should be understood that this depiction is illustrative in nature and that there are myriad ways couple the information output from the analysis module to the provider and patient interfaces described herein, all of which are included within the spirit and scope of the invention FIG. 2 further shows secure data storage module 217, which provides data storage for analysis module 210. A non-limiting example of types of data stored within secure data storage 217 include patient data, laboratory data, laboratory trend data, critical reports, graphical reports, population health reports, specific disease reports, and information from interfacing with outside vendors and third-party healthcare software. In some embodiments, the secure data storage module may store data in relational formats such as SQL databases and/or in non-relational formats such as flat files, self-referential tables and non-relational databases. In other embodiments, all or part of the data stored in the secure data storage module is stored in the form of a cryptographic blockchain ledger. In the blockchain ledger storage embodiment, as appreciated by those skilled in the art, data is stored in blocks that contain a cryptographic hash of the block contents, a timestamp, and the cryptographic hash of the preceding block. Those skilled in the art will appreciate that other blockchain formats can be used with the invention, with more or fewer fields. Blockchain storage has several advantages, including immutability of block contents, verifiability, and permissions control. In some embodiments, the inventive system stores in the blockchain ledger all interactions with providers, patients, EHR software third-party vendors, and other contributors. The use of the blockchain ledger provides an immutable and encrypted ledger of activity that facilitates several potential applications for the laboratory and associated patient databases, including the storage and retrieval of patient records, including laboratory and other patient data. This patent information can be processed into readable information for a patient's own use or converted into encrypted records that can be read by a variety of electronic medical records systems using the patient-specific ID and encryption key. Links to detailed anonymized information about procedures, encounters, diagnoses, claims and prescriptions could be added over time, and access to this information could be managed by the patient or the patient's designees. Another contemplated use of the blockchain ledger in the invention is in clinical trials. Using the blockchain ledger in secure data storage 217, the inventive system can securely share data generated or required by clinical trials, such as patient demographics and information about adverse reactions to treatment. Interim results could be shared with other researchers and regulators. To accomplish transparency and validity of clinical trials, the documents created and used in the process such as informed consent, research plans, regulations and study protocol can be time-stamped by the system. Study results and patient outcome data is advantageously stored on the blockchain ledger, which ensures that the trial documents and outcomes will have a verifiable proof of authenticity with immutable details of their creation time and content, thus, making it nearly impossible for any such clinical trials data to be manipulated or left out of final analyses.

In certain embodiments, secure data storage module 217 provides "big data" analytical capabilities. This capability is useful for external analysis and mining of de-identified data within secure data storage 217 by researchers, third-party experts, clinicians and physicians for identifying gaps in care, the need to follow up on abnormal lab results, to identify those patients that declined follow-up, to identify the number of patients that reviewed their patient enhanced reports, to integrate with health departments and payors, and to follow quality measures for population health and Accountable Care Organization (ACO) mandates. The preceding is a non-limiting list of data analysis purposes and is meant to be illustrative and not exhaustive. As examples, the deidentified data is also useful for research into the following treatment areas: 1) diabetes treatment research, by measurement and tracking of the serum random glucose, the serum hemoglobin A1c, urinalysis findings, and demographic data such as age, sex, height, weight, and medications; 2) kidney research, by measurement and tracking of the serum creatinine level, serum estimated glomerular filtration rate (eGFR), and urine albumin to creatinine ratio, and demographics data; 3) cardiovascular disease states by measurement and tracking of the serum lipid panel that includes total cholesterol, HDL and LDL cholesterol, triglycerides, direct LDL, serum C reactive protein (cRP), CK isoenzymes, Troponin I, brain natriuretic peptide (BNP), as well as NT-proBNP levels; 4) prostate disease research, by measurement and tracking of the serum free and total PSA level, prostatic acid phosphatase levels, and MiII findings; and 5) liver research, by measurement and tracking of the serum AST, ALT, ALP, GGT, bilirubin, PT, PTT, INR levels and imaging and biopsy findings.

Figure 3:
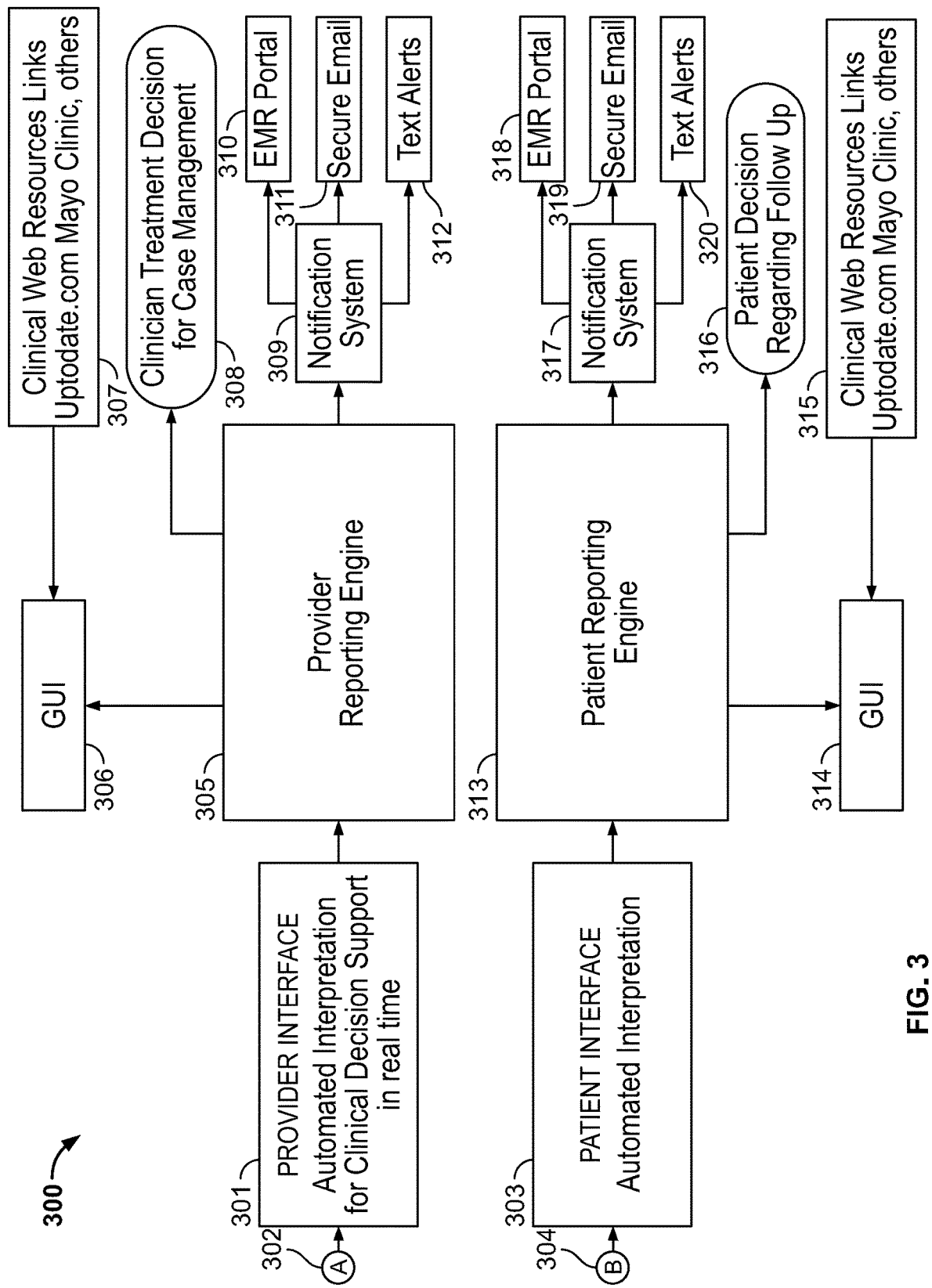
FIG. 3 is a block diagram that depicts an embodiment of the present invention comprising the provider and patient interfaces, the provider and patient reporting engines and various means to communicate results to providers and patients.

FIG. 3 is a block diagram of an embodiment 300 of the invention that illustrates the provider and patient interfaces and provider and patient reporting engines described herein. Provider interface 301 provides automated interpretation of diagnostic test results for clinical decision support in real time received on exemplary input A 302 from analysis module 210. Provider interface 301 processes the raw data produced by analysis module 210 to produce structured data comprising the suggested medical diagnoses and clinical recommendations output by provider reporting engine 305. For example, in one embodiment the provider reporting engine outputs an enhanced report containing the following types of information: 1) Color coded lab data report showing green, yellow and red zones (normal, caution, and critical results); 2) results that are custom triaged into normal, slightly abnormal, urgent, and critical with default and custom user settings for each test; 3) trend graph showing all previous results over time of each test; 4) interpretability of the tests, in whole or in part, and which parts could be interpreted; 5) interpretation of the laboratory tests and condition(s) if possible and based on evidence-based guidelines and major medical societies, along with ICD-10 and HCC codes (see below), such as the American Medical Association, American College of Physicians, American Society of Internal Medicine, American Academy of Family Medicine, American College of Cardiology, American Heart Association, American College of Obstetricians and Gynecologists, American Cancer Society, American Urological Association, and others; 6) reflex, additional lab test recommendations if needed and interface to place additional orders; 7) reflective, additional lab test recommendations if needed and interface to place the additional orders; 8) recommendations for other ancillary testing such as CT, MRI imaging, and other testing; 9) recommendations for possible referral to specific specialties, as dictated by the lab reports, such as hematology/oncology, gastroenterology, nephrology, urology, endocrinology, general surgery, and others, including acute hospitalization; and 10) recommendations for follow up with the patient either STAT (immediate) or specific interval of time for example one week, two weeks, four weeks, 6 weeks, three months and so on. Those skilled in the art will appreciate that additional, or fewer types of information can be included in the provider enhanced report and remain within the scope and spirit of the invention.

In another embodiment, the provider enhanced report produced by provider reporting engine 305 includes 1) laboratory test values of concern; 2) trendlines for the same patient last laboratory test value for any abnormal results in graphical format with commentary regarding the trend; 3) information with color highlights according to the interpretation laboratory test results, e.g., red for results that are severely abnormal and are either of critical or urgent priority, yellow results that are mildly to moderately abnormal and are of either urgent, semi-urgent, or non-urgent priority, and green for normal results; 4) a general laboratory health indicator score with color coding and the percentage of normal test results as well as an indication of what percentage of test results were automatically interpreted; 5) specific interpretations and recommended clinical actions for each laboratory test results, for example, the possible differential diagnoses, consideration of other specific testing, and treatment options for the medical diseases or conditions suggested by the laboratory data; and 6) references to evidence-based guidelines or literature where available for the specific clinical conditions. Those skilled in the art will appreciate that the types of information contained in the enhanced report generated by the provider reporting engine 305 may contain more or fewer types of information than those enumerated and that there are myriad ways to organize the information output from the provider reporting engine described herein, all of which are included within the spirit and scope of the invention.

Selected portions of two exemplary provider enhanced reports produced in one embodiment of the invention are provided below:
1) Initial patient laboratory testing
Laboratory test results:
Hb: 9.0 g/dL (low)
MCV: 75 fL (low)
serum protein: normal range
serum globulin: normal range
Diagnostic Impression:
Results show that the patient is moderately anemic with microcytosis.
Severity level: moderate
Suggested ICD-10 is I50.9

Clinical Recommendations:
Recommend reflective testing to include serum iron, transferrin, ferritin and TIBC. Also consider additional testing to include measurement of Vitamin B12, folate, and hemoglobin electrophoresis to rule out genetic causes of the anemia unless previously performed. Suggest patient have an evaluation for sources of potential blood loss, to include gastrointestinal and genitourinary evaluations if clinically indicated and follow up within one month
Priority level: medium priority
2) The same patient returns for repeat laboratory testing and examination at a future visit:
Laboratory test results:
Hb: 8.0 g/dL (moderately low)
MCV: 72 fL (low)
serum protein: elevated
serum globulin: elevated
Diagnostic Impression:
Results show that the patient is now moderately anemic with progression of the severity. There are new elevations of the serum proteins concerning for hematologic malignancy.
Severity level: moderate
Suggested ICD-10 are I50.9 and E88.09
Clinical Recommendations:
Recommend reflective testing to additionally include SPEP, SPIP, and immunofixation. Also recommend patient have an evaluation for sources of potential blood loss, to include gastrointestinal and genitourinary evaluations if clinically indicated. Recommend hematology consult for possible blood dyscrasia, if clinically indicated, and follow up within one week
Priority level: high priority.

The provider enhanced report can be provided to the clinician in a variety of ways. For example, the clinician can view the enhanced report in a graphical user interface 306 through a network connection such as the Internet. The provider interface notification system 309 can transmit the provider enhanced report or a subset of the information thereof to the provider via 1) an EMR portal 310, 2) secure email 311, or 3) text or SMS alert 312. For example, notification system 309 can be interfaced with the provider's EHR message inbox as selected by the provider notification settings. It is contemplated that the invention will communicate with all major EHR software providers, as well as sending notification email into the provider's email inbox as selected by the provider settings, and/or paging or sending SMS messages to the provider on a cellular device as a notification alert, as selected by the provider settings. The notification system can also alert medical management and/or appointment schedulers. The graphical user interface 306 that is part of the provider portal can also have links to Internet-based content 307 for each major disease or condition that shows evidence-based recommendations such as The U.S. Preventive Services Task Force recommendations, Uptodate.com, National Committee for Quality Assurance (NCQA), Centers for Medicare and Medicaid Services (CMS.gov), and other approved clinical web resources described above. Moreover, the provider reporting engine 305 can produce daily reports with clinician recommendations, a triaged set of data that is prioritized in terms of most severe anomalies or conditions first, and the ability to adjust notification settings. In addition, the provider reporting engine can be used to report care quality issues or to prompt follow-up appointments, eliminate gaps in care for example lack of follow up on abnormal test results, provide annual wellness reminders, tracking trends, scheduling quarterly A1c recall visits for diabetes, asthma visits, CHF visits, tracking of diabetics with nephropathy and chronic kidney disease, and so on.

In certain embodiments, the invention will record the time when the provider reviewed the enhanced report message and the actions taken 308 by the provider if any and record this event on the blockchain ledger. The actions will be stored and tabulated for statistical purposes and used for quality improvement and training of the rules engine 212 in analysis module 210. The inventive system will take all the laboratory results from each patient encounter and apply the AI algorithms in analysis module 210 to return a real-time interpretive report to the provider to improve diagnosis and treatment planning decisions. These recommendations can include any and or all the following comment types and recommendations: 1) comments will be made as to which and what percentage of tests on the report are being interpreted, for example, the system will handle the most commonly and routinely ordered tests for the region and country, however some rarer tests may not be automatically interpreted and will need human review by the ordering provider; 2) some laboratory findings may equate to, or provide direction to, certain provisional diagnoses and or diagnostic category, with corresponding ICD-10 code and/or CMS hierarchical condition code (HCC) relayed to the EMR and added into the Medical History section of the chart; 3) suggestion for reflex testing based on current clinical guidelines; and 4) suggestion for reflective testing, based on current clinical guidelines.

FIG. 3 also depicts patient interface 303, which provides automated interpretation of diagnostic test results for patients received on exemplary input B 304 from analysis module 210. Patient interface 303 processes the raw data produced by analysis module 210 to produce structured data comprising the suggested medical diagnoses and clinical recommendations output by patient reporting engine 313. For example, the patient reporting engine outputs an patient enhanced report containing the following types of information: 1) color-coded lab data report showing green, yellow and red zones (normal, caution, and critical results); 2) results will be also custom triaged into normal, slightly abnormal, urgent, and critical with default and custom user settings for each test; 3) trend graph showing all previous results over time of each test; 4) interpretability of the tests, in whole or in part, and which parts could be interpreted; 5) interpretation of the laboratory tests and condition(s) if possible, using patient friendly explanations; 6) reflex, additional lab test recommendations if needed; 7) reflective, additional lab test recommendations if needed; 8) recommendations for other ancillary testing such as CT, MRI imaging, and other testing; 9) recommendations for possible referral to specific specialties, as dictated by the lab reports, such as hematology/oncology, gastroenterology, nephrology, urology, endocrinology, and others; 10) recommendations for follow up with the provider if outpatient setting, either STAT (immediate visit, or emergency room visit) or specific interval of time for example one week, two weeks, four weeks, 6 weeks, three months etc. Those skilled in the art will appreciate that additional, or fewer types of information can be included in the patient enhanced report and remain within the scope and spirit of the invention.

In another embodiment, the patient enhanced report produced by patient reporting engine 313 includes 1) laboratory test values of concern; 2) trendlines for the same patient last laboratory test value for any abnormal results in graphical format with commentary regarding the trend; 3) information with color highlights according to the interpretation laboratory test results, e.g., red for results that are severely abnormal and are either of critical or urgent priority, yellow results that are mildly to moderately abnormal and are of either urgent, semi-urgent, or non-urgent priority, and green for normal results; 4) a general laboratory health indicator score with color coding and the percentage of normal test results as well as an indication of what percentage of test results were automatically interpreted; and 5) general interpretation of laboratory test results in patient-friendly language, possible diagnoses with ICD-10 classifications and HCC codes, and recommended actions for follow-up with their providers for further disposition, monitoring, investigation and or treatment, as indicated. For example, the patient enhanced report can recommend a routine visit, non-urgent one-month follow-up, semi-urgent two-week follow-up, urgent 72-hour follow-up, or stat/immediate follow-up. Those skilled in the art will appreciate that the types of information contained in the enhanced report generated by the patient reporting engine 313 may contain more or fewer types of information than those enumerated and that there are myriad ways to organize the information output from the patient reporting engine described herein, all of which are included within the spirit and scope of the invention.

Selected portions of two exemplary patient enhanced reports produced in one embodiment of the invention are provided below:

1) Initial patient laboratory testing
Laboratory test results:
TSH: 0.967 (normal)
Free T4: 1.2 (normal)
Free T3: 2.5 (normal)
Anti TPO antibodies: 275 (high)
TSI antibodies: 3 (negative)
Diagnostic Impression:
All lab data was analyzed by Intelligen Lab Analytics.
Overall score: Green zone
The lab results show that your thyroid hormone testing is in the normal range. However, they also show that you may have an autoimmune thyroid condition known has Hashimoto's disease, that may result in temporary inflammation of the thyroid, and either an overactive, or underactive thyroid state in the future.
The thyroid gland is a vital hormone gland: It plays a major role in the metabolism, growth and development of the human body. It helps to regulate many body functions by constantly releasing a steady amount of thyroid hormones into the bloodstream. If the body needs more energy in certain situations—for instance, if it is growing or cold, or during pregnancy—the thyroid gland produces more hormones.
This organ is found at the front of the neck, under the voice box. It is butterfly-shaped: The two side lobes lie against and around the windpipe (trachea) and are connected at the front by a narrow strip of tissue.
Symptoms of an underactive thyroid, known as hypothyroidism, can include fatigue, cold sensitivity, constipation, dry skin, and unexplained weight gain.
Symptoms of an overactive thyroid, known as hyperthyroidism include unexpected weight loss, rapid or irregular heartbeat, sweating, and irritability, although the elderly often experience no symptoms.
Severity level: minimal
Recommended actions: recommend follow up with your provider within three months, or sooner, if you are experiencing any unusual symptoms.

2) The same patient returns for repeat laboratory testing and examination:
Laboratory test results:
TSH: 0.006 (very low)
Free T4: 5.5 (very high)
Free T3: 7.6 (very high)
Diagnostic Impression:
Overall score: Red zone
The lab results show that your thyroid gland is overactive consistent with hyperthyroidism related to your known condition of Hashimoto's disease
Symptoms of an underactive thyroid, known as hypothyroidism, can include fatigue, cold sensitivity, constipation, dry skin, and unexplained weight gain.
Symptoms of an overactive thyroid, known as hyperthyroidism include unexpected weight loss, rapid or irregular heartbeat, sweating, and irritability, although the elderly often experience no symptoms.
Severity level: moderate
Recommended actions: Recommend urgent follow up with your provider within one week, or sooner if you are experiencing any symptoms. Results require provider to review potential treatment options that may include medications to help slow the thyroid down and other medications such as beta blockers.
You may also benefit from seeing a specialist in endocrinology, if your provider believes it is necessary.

The patient enhanced report can be provided to the patient in a variety of ways. For example, the patient can view the enhanced report in patient graphical user interface 314 through a network connection such as the Internet. The patient interface notification system 317 can transmit the patient enhanced report or subset thereof to the patient via 1) an appointment request tool in an EMR portal 318; 2) secure email 319, or 3) text or SMS alert 320. For example, notification system 317 can be interfaced with the patient's EHR/EMR portal inbox and/or private email inbox as selected by the patient's notification settings. Notification system 317 can also send SMS messages to the patient on a cellular device as a notification alert, as selected by the patient's notification settings. The graphical user interface 314 that is part of the patient reporting engine 313 can also have links to Internet-based content 315 for each major disease or condition such as Uptodate.com, the Mayo Clinic, Familypractice.com, Wikipedia, and other approved clinical web resources for patients or approved search engines. Moreover, the patient reporting engine 313 can provide the patient with a real-time report containing recommendations after each lab report is ready and a triaged set of data that is prioritized in terms of most severe anomalies or conditions first, and the ability to adjust notification settings.

The inventive system will record the time when the patient reviewed the message and the actions 316 taken by the patient if any and record this event on the blockchain ledger. For example, the patient can directly interface and communicate or call with the provider office and make a follow up appointment. The actions are stored and tabulated for statistical purposes and used for quality improvement and training of analysis module 210.

The present invention is an expert system that evolves and self-learns over time. The interpretive comments and recommendations will be based on currently accepted practice guidelines and practice patterns in the region and country of the providers' practice, and evidence-based recommendations. The conclusions and recommendations made by the system will be reviewed and enhanced over time using input from the user (provider) level, as well as Experts in clinical diagnostic, clinical chemistry, pathology, and other specialties that will focus on each of their respective laboratory expertise. User-level feedback is provided as each provider can agree or disagree with the interpretive comments and clinical recommendations, if any, made by the system at each patient encounter. The system will then track these responses and increase the strength/weight of the recommendations as appropriate in future encounters to represent a peer-reviewed consensus of the recommendations for each specific disease or condition identified and the associated clinical recommendations as well. For example, at the end of the report the provider has the option to agree or disagree with each recommendation, with a weighting scale from one to five, using a Likert-like scoring system, (1=Strongly Disagree, 2=Disagree, 3=Neutral, 4=Agree, 5=Strongly Agree). Thus, the system will automatically "learn" which interpretations are the "best" and most widely accepted for the region's practice patterns, and display this "peer-reviewed" weight on future recommendations. This numerical rating system is fed back to the analysis module and used in the quality review program of the analysis module automatically. The system will also allow users and providers to attach a message back to the system administrator, for expert consideration at quality review meetings. If there are unusual patterns or rejections, these will be appropriately flagged to the expert consultants for more immediate attention and review by human reviewers using the knowledge base editor, rules engine editor, or both. Furthermore, the system automatically recognizes and learns what interpretive recommendations are being accepted by the medical community at large for the specific region and country involved adding weight and reinforcing all the "correct" recommendations and flagging the unaccepted recommendations for expert internal review and quality improvement.

The invention will benefits providers, clinics, and hospitals participating in the Medicare Value Based Compensation Models in that the laboratory data used to report quality for the population health improvement aim to the Center for Medicare and Medicaid Services (CMS) will be automatically captured, flagged and reported to the providers. For example, for primary care providers who furnish service to Medicare Beneficiaries, one of the key quality performance indicators for 2018 is an outcome measure assessment that looks at effective treatment of Hemoglobin A1c in diabetic patients. The system will automatically capture, flag and report all normal and abnormal reports for this Medicare quality outcome measure. The inventive system will be able to flag all patient charts if their A1c results are greater than the current quality goal of 9.0% or less. The system will also remind the provider to reorder the test at an appropriate interval of time in the future, for example 3 months, in order to meet the goal for the calendar year. It will also produce a report of all patients that have met goal and who have not met goals. As another example, for primary care and other providers, another quality measure for medical processes evaluates provider's success rate at screening for and capturing diabetic nephropathy during the calendar year. This is generally achieved by ordering the appropriate lab tests for serum creatinine and urine albumin/creatinine ratio, previously referred to as the urine microalbumin level or urine microalbumin/creatinine ratio. The system will automatically capture, flag and report all normal and abnormal reports for this Medicare quality process measure. If abnormal, the system will remind the provider to reorder the test at an appropriate interval of time in the future, for example 3 months, keeping with best clinical practices and meeting the calendar year screening guidelines. Similarly, the system facilitates adding or editing additional laboratory parameters that will be essential for quality reporting in the future for CMS reporting as well as any quality initiatives set forth by commercial insurance payors in the future.

Figure 4:
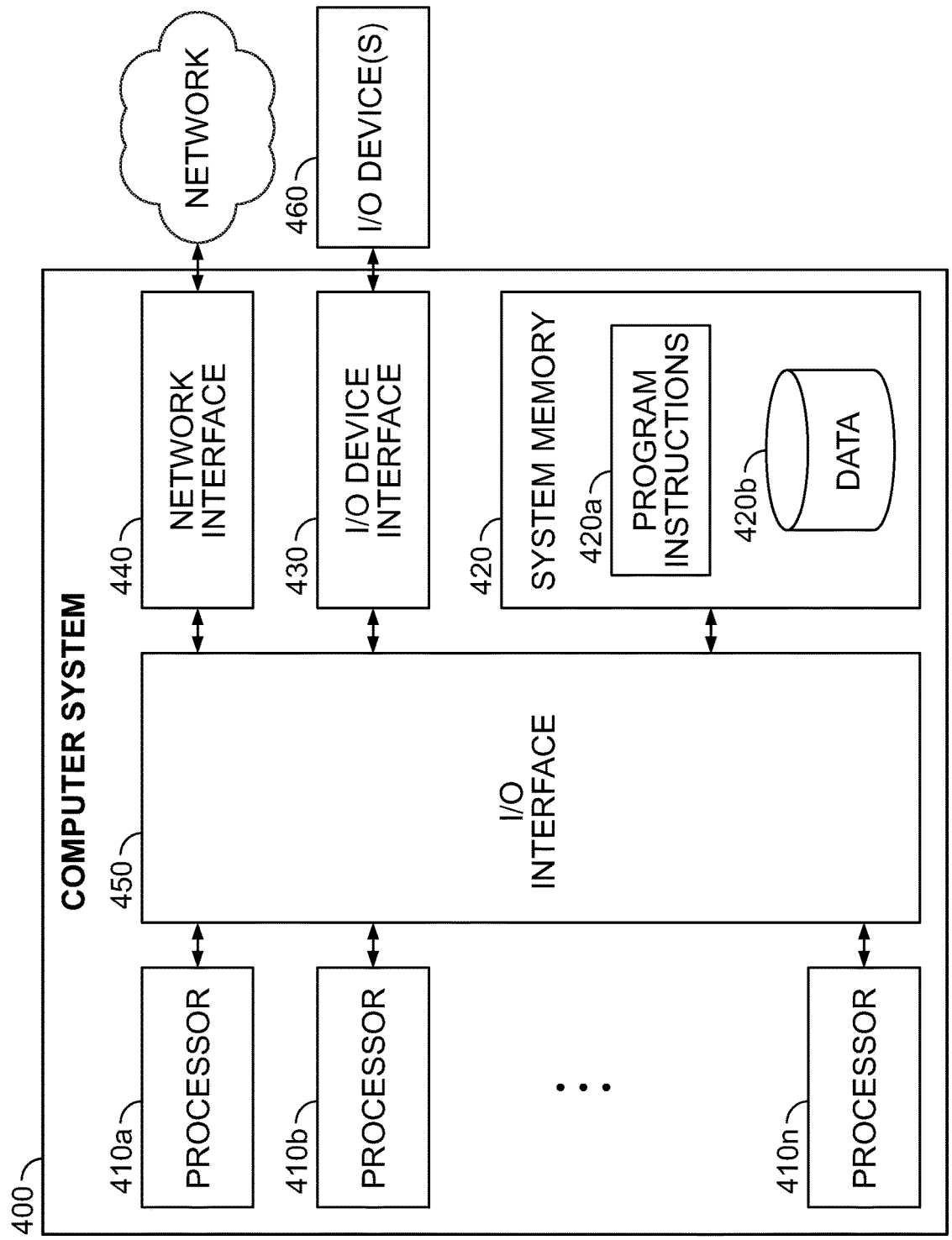
FIG. 4 depicts an exemplary computer system by which some embodiments are implemented.

FIG. 4 is a diagram that illustrates an exemplary computing system 400 in accordance with embodiments of the present techniques. Various portions of systems and methods described herein, may include or be executed on one or more computer systems like computing system 400. Further, processes and modules described herein may be executed by one or more processing systems like that of computing system 400.

Computing system 400 may include one or more processors (e.g., processors 410a-410n) coupled to system memory 420, an input/output I/O device interface 430, and a network interface 440 via an input/output (I/O) interface 450. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 400. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 420). Computing system 400 may be a uni-processor system including one processor (e.g., processor 410a), or a multi-processor system including any number of suitable processors (e.g., 410a-410n). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 400 may include a plurality of computing devices (e.g., distributed computer systems) to implement various processing functions.

I/O device interface 430 may provide an interface for connection of one or more I/O devices 460 to computer system 400. I/O devices may include devices that receive input (e.g., from a user) or output information (e.g., to a user). I/O devices 460 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 460 may be connected to computer system 400 through a wired or wireless connection. I/O devices 460 may be connected to computer system 400 from a remote location. I/O devices 460 located on remote computer system, for example, may be connected to computer system 400 via a network and network interface 440.

Network interface 440 may include a network adapter that provides for connection of computer system 400 to a network. Network interface 440 may facilitate data exchange between computer system 400 and other devices connected to the network. Network interface 440 may support wired and/or wireless communication. The network may include an electronic communication network, such as the Internet, a local area network (LAN), a personal area network (PAN), a near field communication network (NFC), a wide area network (WAN), a cellular communications network, or the like.

System memory 420 may be configured to store program instructions 420a or data 420b. Program instructions 420a may be executable by a processor (e.g., one or more of processors 410a-410n) to implement one or more embodiments of the present techniques. Instructions 420a may include modules of computer program instructions for implementing one or more techniques described herein regarding various processing modules. Program instructions may include a computer program (which in certain forms is known as a program, application, software, software application, applet, plug-in, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 420 may include a tangible program carrier having program instructions stored thereon. A tangible program carrier may include a non-transitory computer readable storage medium. A non-transitory computer readable storage medium may include a machine-readable storage device, a machine-readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random-access memory (SRAM), synchronous dynamic RAM (SDRAM)), bulk storage memory (e.g., CD-ROM and/or DVD-ROM, hard-drives), or the like. System memory 420 may include a non-transitory computer readable storage medium that may have program instructions stored thereon that are executable by a computer processor (e.g., one or more of processors 410a-410n) to cause the subject matter and the functional operations described herein. A memory (e.g., system memory 420) may include a single memory device and/or a plurality of memory devices (e.g., distributed memory devices).

I/O interface 450 may be configured to coordinate I/O traffic between processors 410a-410n, system memory 420, network interface 440, I/O devices 460, and/or other peripheral devices. I/O interface 450 may perform protocol, timing, or other data transformations to convert data signals from one component (e.g., system memory 420) into a format suitable for use by another component (e.g., processors 410a-410n). I/O interface 450 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 400 or multiple computer systems 400 configured to host different portions or instances of embodiments. Multiple computer systems 400 may provide for parallel or sequential processing/execution of one or more portions of the techniques described herein.

Those skilled in the art will appreciate that computer system 400 is merely illustrative and is not intended to limit the scope of the techniques described herein. Computer system 400 may include any combination of devices or software that may perform or otherwise provide for the performance of the techniques described herein. For example, computer system 400 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 400 may also be connected to other devices that are not illustrated or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Figure 5:
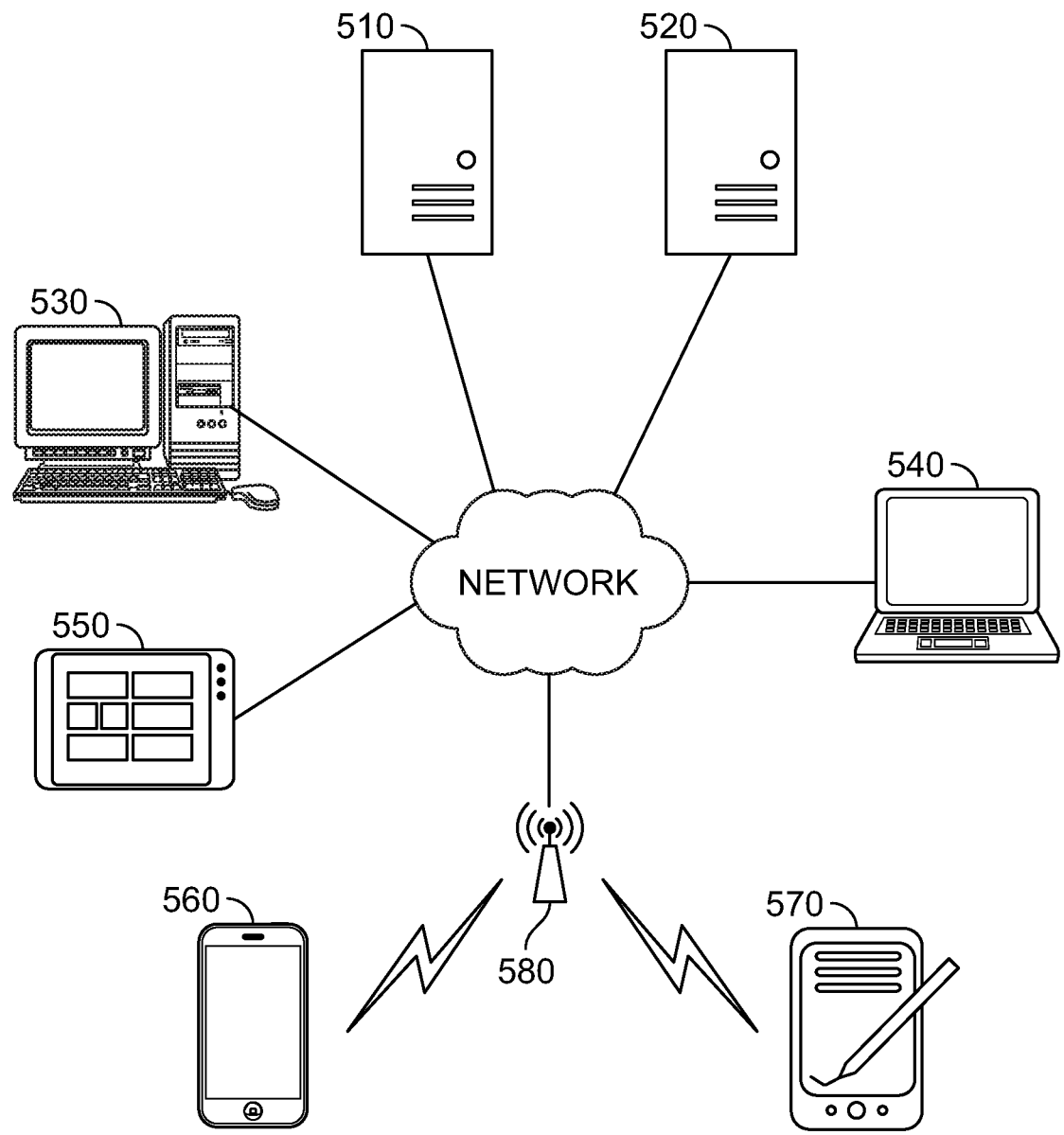
FIG. 5 depicts a network diagram with exemplary networked computing systems by which some embodiments are implemented.

FIG. 5 is a network diagram that illustrates exemplary computing systems in communication with one or more computing systems in network 500 to implement enhanced security systems in accordance with embodiments of the present technique. Various portions of the systems and methods described herein may include implementation on one or more computing systems depicted in network 500. For example, it is contemplated that the invention can be implemented completely on any exemplary device depicted in FIG. 5, including server computers 510 and 520, desktop computer 530, notebook computer 540, tablet 550, smartphone 560, or personal digital assistant (PDA) 570. However, the invention may also be advantageously implemented on two or more of the exemplary devices depicted in FIG. 5. Although the network 500 is depicted without detail of specific network implementations save for wireless access point 580, those skilled in the art should understand that the invention is not limited by any particular network configuration, and indeed the invention is flexible enough to be implemented in the context of any network type or configuration, including local area networks (LAN), wide area networks (WAN), personal area networks (PAN), and wireless networks of various types including LANs, WANs, and PANs. For example, in a client-server embodiment, any of client devices comprising desktop computer 530, notebook computer 540, tablet 550, smartphone 560, or personal digital assistant (PDA) 570 can implement any part of the invention described herein, with the remainder of the invention implemented on either or both server computers 510 and 520. In one embodiment, server computers 510 and/or 520 implement all of the inventive system. In a cloud computing environment, the inventive system can be distributed over any number of server computers, with the same or different roles for each server. Those skilled in the art will appreciate the myriad configurations and scenarios of both devices and networks possible with the invention, all of which are intended to be within the spirit and scope of the invention.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 400 may be transmitted to computer system 400 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present invention may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several inventions. Rather than separating those inventions into multiple isolated patent applications, applicant has grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to cost constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

What is claimed is:

1. A method for automated medical diagnostic analysis, comprising:
   a computing system with one or more processors performing the steps of:
   receiving laboratory test results in numerical and textual form for one or more routine diagnostic laboratory tests performed on a patient as ordered by a clinician;
   receiving protected health information for said patient, where said protected health information includes patient demographic data including the patient's address;
   storing said laboratory test results and said protected health information for said patient in a secure data storage system, wherein said secure data storage system stores the test results and protected health information in a cryptographic blockchain ledger;
   determining a region and country where the patient is located from the patient's address;
   comparing said laboratory test results for said patient with reference information contained in a knowledge base in numerical and textual form and creating one or more initial diagnostic interpretations for said patient based on the laboratory results comparison;
   comparing the reference information with reference ranges specific to the region and country where the patient is located and modifying the one or more initial diagnostic interpretations for said patient based on the reference ranges comparison, wherein the modifying produces one or more modified diagnostic interpretations different from the one or more initial diagnostic interpretations, and wherein the reference ranges specific to the region and country are contained in the knowledge base;
   analyzing said one or more modified diagnostic interpretations with one or more machine learning algorithms to produce one or more determined medical diagnoses, the severity level for each of said one or more determined medical diagnoses, one or more clinical recommendations and an overall priority level for said patient, wherein the one or more machine learning algorithms utilize weighted nodes, and wherein said one or more determined medical diagnoses are produced in patient-appropriate language and clinician-appropriate language;
   storing in said secure data storage system said one or more modified diagnostic interpretations, said one or more determined medical diagnoses, said severity level for each of said one or more determined medical diagnoses, said one or more clinical recommendations, and said overall priority level for said patient;
   providing a clinician diagnostic report to said clinician comprising said laboratory test results, said one or more modified diagnostic interpretations, said one or more determined medical diagnoses in the clinician-appropriate language, said severity level for each of said one or more determined medical diagnoses, said one or more clinical recommendations and said overall priority level for said patient;

providing a patient diagnostic report to said patient comprising said laboratory test results, said one or more determined medical diagnoses in the patient-appropriate language, said severity level for each of said one or more determined medical diagnoses, an overall score, and one or more recommended actions for said patient;

receiving diagnosis feedback from said clinician in the form of a numerical diagnosis weighting scale for at least one of said one or more modified diagnostic interpretations and at least one of said one or more determined medical diagnoses for said patient, wherein the diagnosis feedback is specific to the region and country where the patient is located;

receiving clinical recommendation feedback from said clinician in the form of a numerical clinical recommendation weighting scale for at least one of said one or more clinical recommendations for said patient, wherein the clinical recommendation feedback is specific to the region and country where the patient is located;

modifying said one or more machine learning algorithms used for subsequent determination of diagnostic interpretations and determined medical diagnoses bar increasing or decreasing the weights applied to the weighted nodes of each of the one or more machine learning algorithms according to the received diagnosis feedback that is specific to the region and country where the patient is located; and modifying said one or more machine learning algorithms used for subsequent determination of clinical recommendations by increasing or decreasing the weights applied to the weighted nodes of each of the one or more machine learning algorithms according to the received recommendation feedback that is specific to the region and country where the patient is located.

2. The method of claim 1, wherein one of said one or more machine learning algorithms is a supervised machine learning algorithm implemented in an analytical rules engine.

3. The method of claim 2, wherein said supervised machine learning algorithm is one of rules-based systems, decision trees, logical conditions, causal probabilistic networks, Bayesian networks, support vector machines, neural networks and genetic networks.

4. The method of claim 3, wherein said secure data storage system stores identified and de-identified health data.

5. The method of claim 4, wherein said secure data storage system stores a subset of data in a cryptographic blockchain ledger.

6. The method of claim 4, wherein said secure data storage system stores all data in a cryptographic blockchain ledger.

7. The method of claim 3, wherein said supervised machine learning algorithm is self-learning as diagnostic interpretations are analyzed to produce determined medical diagnoses based on laboratory test results for one or more patients.

8. A system for automated medical diagnostic analysis comprising:

a computing system with one or more processors receiving laboratory test results in numerical and textual form for one or more routine diagnostic laboratory tests performed on a patient as ordered by a clinician and receiving protected health information for said patient, wherein said protected health information includes patient demographic data including the patient's address, and determining a region and country where the patient is located from the patient's address, further comprising:

a knowledge base comprised of data representing medical reference information in numerical and textual form to compare to said laboratory test results for one or more diagnostic laboratory tests performed on said patient to create one or more initial diagnostic interpretations for said patient based on the laboratory test results comparison, and further to compare the reference information with reference ranges specific to the region and country where the patient is located and modifying the one or more initial diagnostic interpretations for said patient based on the reference ranges comparison, wherein the modifying produces one or more modified diagnostic interpretations different from the one or more initial diagnostic interpretations, and wherein the reference ranges specific to the region and country are contained in the knowledge base;

an analytical rules engine employing one or more artificial intelligence machine learning algorithms to analyze said one or more modified diagnostic interpretations to produce one or more determined medical diagnoses, the severity level for each of said one or more determined medical diagnoses, one or more clinical recommendations and an overall priority level for said patient, wherein the one or more machine learning algorithms utilize weighted nodes, and wherein said one or more determined medical diagnoses are produced in patient-appropriate language and clinician-appropriate language;

a provider interface providing a clinician diagnostic report to said clinician comprising said laboratory test results, said one or more modified diagnostic interpretations, said one or more determined medical diagnoses in the clinician-appropriate language, said severity level for each of said one or more determined medical diagnoses, said one or more clinical recommendations and said overall priority level for said patient;

a patient interface providing a patient diagnostic report to said patient comprising said laboratory test results, said one or more determined medical diagnoses in the patient-appropriate language, said severity level for each of said one or more determined medical diagnoses, an overall score, and one or more recommended actions for said patient;

a feedback interface receiving diagnosis feedback from said clinician in the form of a numerical diagnosis weighting scale for at least one of said one or more modified diagnostic interpretations and at least one of said one or more determined medical diagnoses, wherein the diagnosis feedback is specific to the region and country where the patient is located, and further receiving clinical recommendation feedback from said clinician in the form of a numerical clinical recommendation weighting scale for at least one of said one or more clinical recommendations, wherein the clinical recommendation feedback is specific to the region and country where the patient is located, wherein said analytical rules engine processes said diagnosis feedback to modify one or more artificial intelligence machine learning algorithms used for subsequent determination of diagnostic interpretations and determined medical diagnoses by increasing or decreasing the weights applied to the weighted nodes of each of the one or more machine learning algorithms according to the received diagnosis feedback that is specific to the region and country where the patient is located and further processes said clinical recommendation feedback to modify one or more artificial intelligence machine learning algorithms used for subsequent determination of clinical recommendations by increasing or decreasing the weights applied to the weighted nodes of each of the one or more machine learning algorithms according to the received recommendation feedback that is specific to the region and country where the patient is located; and
- a secure data storage system storing said laboratory test results, said protected health information for said patient; said one or more modified diagnostic interpretations, said one or more determined medical diagnoses, said severity level for each of said one or more determined medical diagnoses, said one or more clinical recommendations and said overall priority level for said patient, wherein the secure data storage system stores secure data in a cryptographic blockchain ledger.

9. The system of claim 8, wherein one of said one or more machine learning algorithms in said analytical rules engine is a supervised machine learning algorithm.

10. The system of claim 9, wherein said supervised machine learning algorithm is one of rules-based systems, decision trees, logical conditions, causal probabilistic networks, Bayesian networks, support vector machines, neural networks and genetic networks.

11. The system of claim 10, wherein said secure data storage system stores identified and de-identified health data.

12. The system of claim 11, wherein said secure data storage system stores a subset of data in a cryptographic blockchain ledger.

13. The system of claim 11, wherein said secure data storage system stores all data in a cryptographic blockchain ledger.

14. The system of claim 10, wherein said supervised machine learning algorithm is self-learning as diagnostic interpretations are analyzed to produce determined medical diagnoses based on laboratory test results for one or more patients.

15. A tangible, non-transitory, machine-readable medium storing instructions that when executed by one or more processors effectuate operations comprising:
- receiving laboratory test results in numerical and textual form for one or more routine diagnostic laboratory tests performed on a patient as ordered by a clinician;
- receiving protected health information for said patient, wherein said protected health information includes patient demographic data including the patient's address;
- storing said laboratory test results and said protected health information for said patient in a secure data storage system, wherein said secure data storage system stores the laboratory test results and protected health information in a cryptographic blockchain ledger;
- determining a region and country where the patient is located from the patient's address;
- comparing said laboratory test results for said patient with reference information contained in a knowledge base in numerical and textual form and creating one or more initial diagnostic interpretations for said patient based on the laboratory test results comparison;
- comparing the reference information with reference ranges specific to the region and country where the patient is located and modifying the one or more initial diagnostic interpretations for said patient based on the reference ranges comparison, wherein the modifying produces one or more modified diagnostic interpretations different from the one or more initial diagnostic interpretations, and wherein the reference ranges specific to the region and country are contained in the knowledge base;
- analyzing said one or more modified diagnostic interpretations with one or more machine learning algorithms to produce one or more determined medical diagnoses, the severity level for each of said one or more determined medical diagnoses, one or more clinical recommendations, and an overall priority level for said patient, wherein the one or more machine learning algorithms utilize weighted nodes, and wherein said one or more determined medical diagnoses are produced in patient-appropriate language and clinician-appropriate language;
- storing in said secure data storage system said one or more modified diagnostic interpretations, said one or more determined medical diagnoses, said severity level for each of said one or more determined medical diagnoses, said one or more clinical recommendations, and said overall priority level for said patient in said secure data storage system;
- providing a clinician diagnostic report to said clinician comprising said laboratory test results, said one or more modified diagnostic interpretations, said one or more determined medical diagnoses in the clinician-appropriate language, said severity level for each of said one or more determined medical diagnoses, said one or more clinical recommendations and said overall priority level for said patient;
- providing a patient diagnostic report to said patient comprising said laboratory test results, said one or more determined medical diagnoses in the patient-appropriate language, said severity level for each of said one or more determined medical diagnoses, an overall score, and one or more recommended actions for said patient; and
- receiving diagnosis feedback from said clinician in the form of a numerical diagnosis weighting scale for at least one of said one or more modified diagnostic interpretations and at least one of said one or more determined medical diagnoses for said patient, wherein the diagnosis feedback is specific to the region and country where the patient is located;
- receiving clinical recommendation feedback from said clinician in the form of a numerical clinical recommendation weighting scale for at least one of said one or more clinical recommendations for said patient, wherein the clinical recommendation feedback is specific to the region and country where the patient is located;
- modifying said one or more machine learning algorithms used for subsequent determination of diagnostic interpretations and determined medical diagnoses by increasing or decreasing the weights applied to the weighted nodes of each of the one or more machine learning algorithms according to the received diagnosis feedback that is specific to the region and country where the patient is located; and modifying said one or more machine learning algorithms used for subsequent determination of clinical recommendations by increasing or decreasing the weights applied to the weighted nodes of each of the one or more machine learning algorithms according to the received recommendation feedback that is specific to the region and country where the patient is located.

16. The medium of claim 15, wherein one of said one or more machine learning algorithms is a supervised machine learning algorithm implemented in an analytical rules engine.

17. The medium of claim 16, wherein said supervised machine learning algorithm is one of rules-based systems, decision trees, logical conditions, causal probabilistic networks, Bayesian networks, support vector machines, neural networks and genetic networks.

18. The medium of claim 15, wherein said secure data storage system stores identified and de-identified health data.

19. The medium of claim 18, wherein said secure data storage system stores a subset of data in a cryptographic blockchain ledger.

20. The medium of claim 17, wherein said supervised machine learning algorithm is self-learning as diagnostic interpretations are analyzed to produce determined medical diagnoses based on laboratory test results for one or more patients.

* * * * *